(12) United States Patent
Heide et al.

(10) Patent No.: US 9,308,312 B2
(45) Date of Patent: Apr. 12, 2016

(54) DEVICE AND METHOD FOR MONITORING AN ACCESS TO A PATIENT

(75) Inventors: Alexander Heide, Eppstein (DE); Jürgen Klewinghaus, Oberursel (DE); Wolfram Langkau, Steinbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 807 days.

(21) Appl. No.: 12/673,811

(22) PCT Filed: Aug. 20, 2008

(86) PCT No.: PCT/EP2008/006841
§ 371 (c)(1),
(2), (4) Date: Mar. 24, 2010

(87) PCT Pub. No.: WO2009/024333
PCT Pub. Date: Feb. 26, 2009

(65) Prior Publication Data
US 2011/0021967 A1    Jan. 27, 2011

(30) Foreign Application Priority Data
Aug. 22, 2007 (DE) .......................... 10 2007 039 581

(51) Int. Cl.
*A61M 37/00* (2006.01)
*A61M 1/36* (2006.01)
(Continued)

(52) U.S. Cl.
CPC ............ *A61M 1/3656* (2014.02); *A61B 5/1411* (2013.01); *A61M 1/3653* (2013.01);
(Continued)

(58) Field of Classification Search
CPC ............. A61B 5/1411; A61M 1/3653; A61M 2205/581; A61M 2205/13; A61M 2205/15; A61M 2205/3375; A61M 2205/44; A61M 5/16836; A61M 2001/3656; A61M 2001/3661; A61M 1/3656; A61M 1/6661; A61M 5/3286; A61M 5/329; A61M 5/3291
USPC .......................................................... 604/6.01
See application file for complete search history.

(56) References Cited

U.S. PATENT DOCUMENTS 5,328,460 A * 7/1994 Lord et al. ...................... 604/67
5,662,619 A * 9/1997 Zarate ............................ 604/272
(Continued)

FOREIGN PATENT DOCUMENTS

| FR | 2788222 A1 | 7/2000 |
| WO | 97/10013 | 3/1997 |

(Continued)

OTHER PUBLICATIONS

International Search Report, PCT/EP2008/006841, mailed Dec. 4, 2008.
(Continued)

*Primary Examiner* — Philip R Wiest
*Assistant Examiner* — Ariana Zimbouski
(74) *Attorney, Agent, or Firm* — Kenyon & Kenyon LLP

(57) ABSTRACT

The present invention relates to a device and a method for monitoring a patient access, particularly for monitoring the venous vascular access in extracorporeal blood treatment where blood is withdrawn from the patient via a flexible arterial line which has an arterial needle or cannula, and provided to the patient via a flexible venous line which has a venous needle or cannula. The needle or cannula of the present invention is so designed that, due to the liquid flowing through the needle or cannula, air is drawn in if the needle or cannula is out of the vascular access, whereby sound is generated. A vascular access which is not in proper order is detected with great certainty and reliability by monitoring the surrounding environment for the occurrence of sound, particularly for the occurrence of the solid-borne sound which propagates along the flexible venous line of the extracorporeal blood circuit.

13 Claims, 3 Drawing Sheets

(51) Int. Cl.
*A61B 5/15* (2006.01)
*A61M 5/168* (2006.01)

(52) U.S. Cl.
CPC ......... *A61M1/3661* (2014.02); *A61M 5/16836* (2013.01); *A61M 2205/13* (2013.01); *A61M 2205/15* (2013.01); *A61M 2205/3375* (2013.01); *A61M 2205/44* (2013.01); *A61M 2205/581* (2013.01)

(56) References Cited

U.S. PATENT DOCUMENTS

| | | | |
|---|---|---|---|
| 7,040,142 B2 * | 5/2006 | Burbank | 73/40 |
| 8,152,751 B2 * | 4/2012 | Roger et al. | 604/4.01 |
| 2003/0126910 A1 | 7/2003 | Burbank | |
| 2003/0128125 A1 * | 7/2003 | Burbank et al. | 340/605 |
| 2004/0054315 A1 | 3/2004 | Levin et al. | |
| 2004/0116879 A1 * | 6/2004 | Mascitelli et al. | 604/272 |
| 2004/0254513 A1 | 12/2004 | Shang et al. | |
| 2006/0135907 A1 | 6/2006 | Remde et al. | |
| 2008/0281219 A1 * | 11/2008 | Glickman et al. | 600/533 |
| 2009/0187164 A1 * | 7/2009 | Rowe | 604/529 |
| 2009/0308387 A1 * | 12/2009 | Andersen et al. | 128/203.15 |
| 2012/0059354 A1 * | 3/2012 | Zarate | 604/506 |

FOREIGN PATENT DOCUMENTS

| | | |
|---|---|---|
| WO | 03/058608 A2 | 7/2003 |
| WO | 2004/110528 A1 | 12/2004 |

OTHER PUBLICATIONS

International Preliminary Report on Patentability, PCT/EP2008/006841, dated Mar. 2, 2010.

* cited by examiner

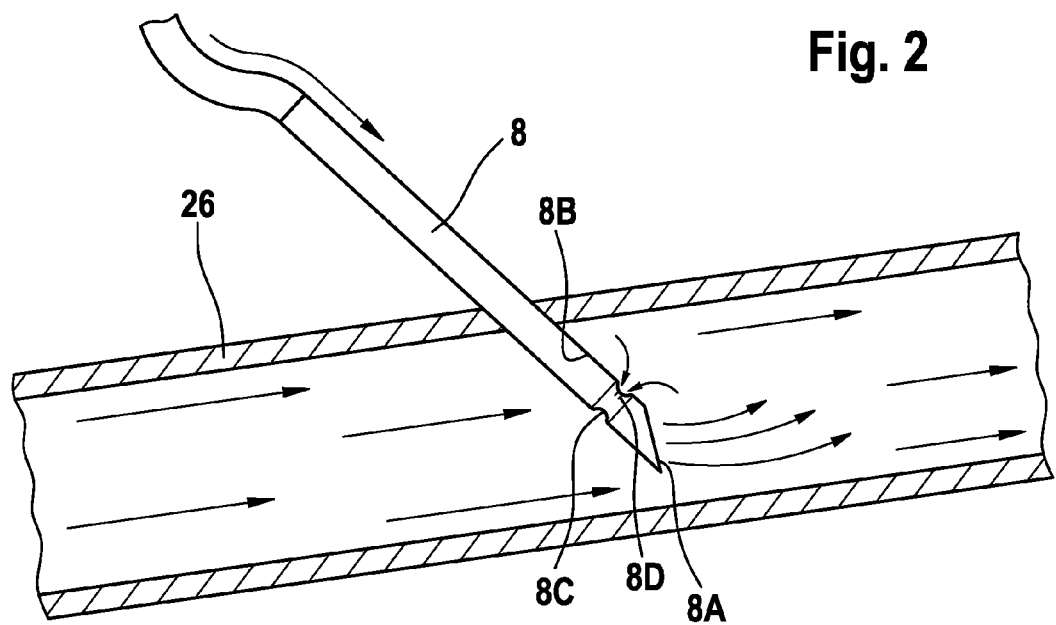
Fig. 2
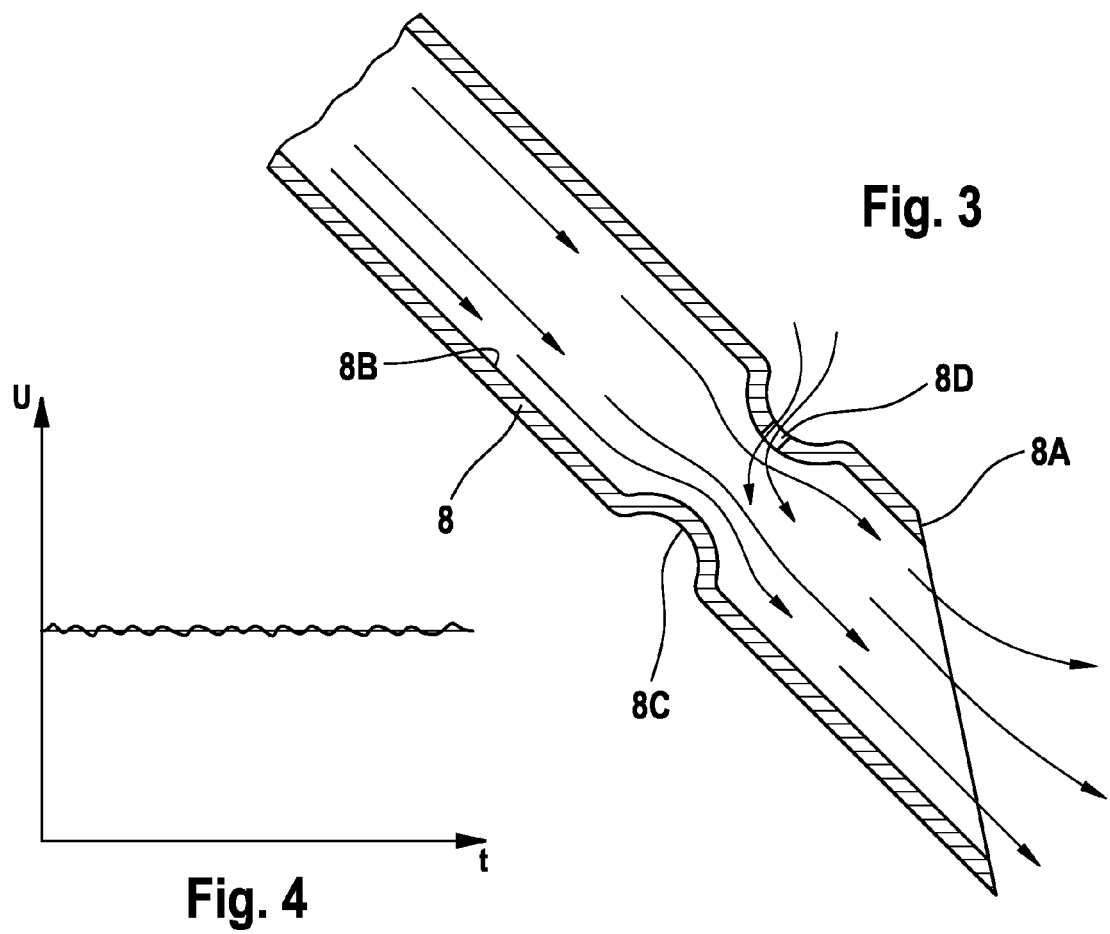
Fig. 3
Fig. 4

Fig. 5
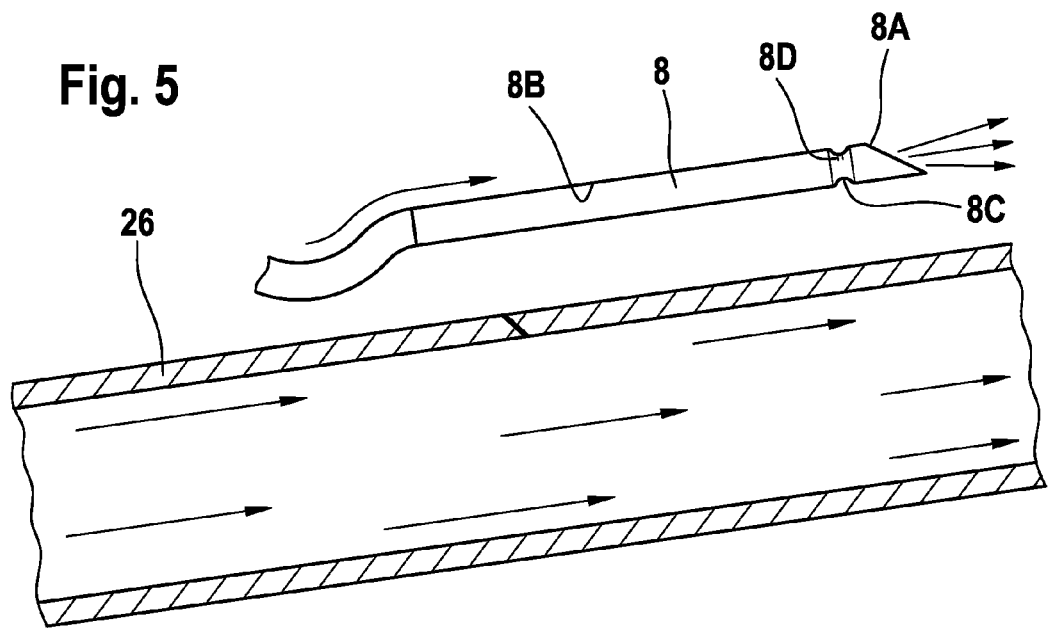
Fig. 6
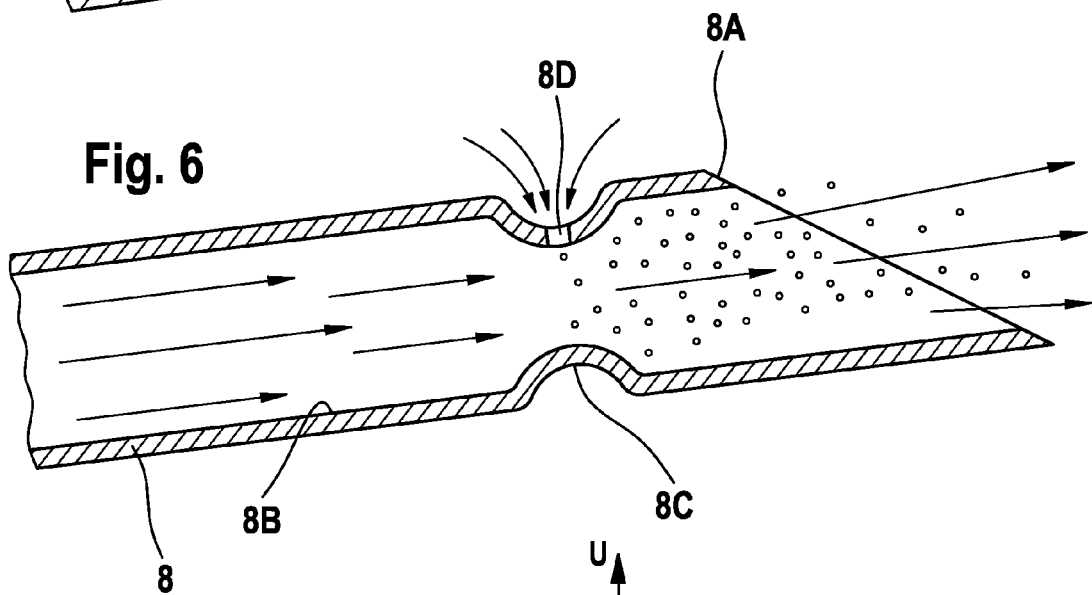
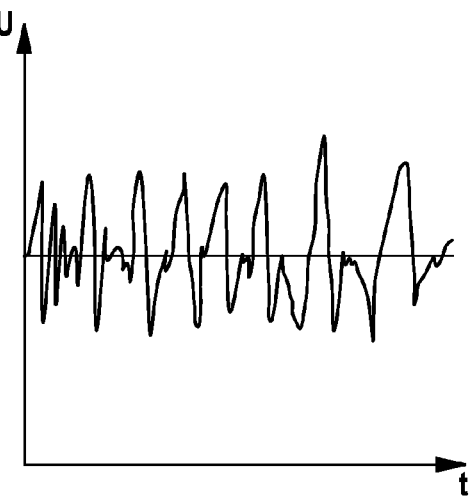
Fig. 7

DEVICE AND METHOD FOR MONITORING AN ACCESS TO A PATIENT

CROSS REFERENCE TO RELATED APPLICATIONS

This is a 371 national phase application of PCT/EP2008/006841 filed Aug. 20, 2008, claiming priority to German Patent Application No. 10 2007 039 581.9 filed Aug. 22, 2007.

FIELD OF INVENTION

The present invention relates to a device for monitoring an access to a patient for an apparatus by which a liquid is provided to the patient via a needle or cannula, and particularly for monitoring the venous vascular access in the case of extracorporeal blood treatment where blood is withdrawn from the patient via a flexible arterial line which has an arterial needle or cannula and blood is provided to the patient via a flexible venous line which has a venous needle or cannula. The present invention also relates to a blood treatment apparatus which has an extracorporeal blood circuit and which has a device for monitoring the venous vascular access. The present invention further relates to a method for monitoring a vascular access.

BACKGROUND OF THE INVENTION

In the field of medical technology, pieces of apparatus are known by which liquids can be withdrawn from a patient and liquids can be provided to the patient. The access to the patient may be gained with a needle or cannula for puncturing vessels in this case. During the examination or treatment, it has to be ensured that the access to the patient remains in proper order. It is therefore necessary for the access to the patient to be monitored.

An application where the safety and reliability of the vascular access has to meet particularly stringent requirements is extracorporeal blood treatment in which blood is withdrawn from the patient via an arterial blood line which has an arterial puncturing needle or cannula, the blood is passed through a dialyser, and is provided back to the patient via a venous blood line which has a venous puncturing needle or cannula. Even though the access to the patient may be regularly monitored by the hospital staff, there is, still a risk in this case that the venous needle or cannula may slip out of the patient's blood vessel unnoticed. Although slipping-out of the arterial cannula causes air to be drawn into the flexible arterial line, which causes an alarm to be given and the treatment to be interrupted; slipping-out of the venous cannula allows for the free flow of blood into the surrounding environment and cannot readily be detected. However, if the slipping-out of the venous cannula is not detected, the patient may bleed to death.

There are different arrangements known in the prior art for solving this problem. Some of these arrangements have recourse to safety devices which are fitted as standard to blood treating machines and trigger an immediate shut-off of the extracorporeal blood circuit if the vascular access is not properly in order. The safety devices which are fitted as standard to treating machines are generally based on monitoring of the pressure in the extracorporeal blood circuit. However, it has been found in practice that slipping-out, particularly of the venous needle or cannula, cannot be detected with sufficient certainty simply by monitoring the pressure in the extracorporeal blood circuit. It is true that some known safety devices are of adequate sensitivity, but they are also very sensitive in the way they react to changes in the patient's position, which often results in false alarms. Another disadvantage is that existing blood treating machines cannot readily be retrofitted with the known monitoring facilities and instead retrofitting calls for laborious and cost-intensive operations to be carried out on the machines.

Known from US 2004/0254513 A1 is an extracorporeal blood treatment apparatus having an extracorporeal blood circuit, which blood treatment apparatus has a monitoring apparatus for the arterial and venous vascular accesses. This known monitoring apparatus has two electrodes, one of which is arranged on the flexible arterial line and the other of which is arranged on the flexible venous line, to make an electrical connection between the liquid in the given flexible line and a monitoring unit. The monitoring unit measures the impedance between the two electrodes, it being concluded that the vascular access is not in proper order if the impedance is not within preset limits. A disadvantage is the fact that the monitoring of the vascular access makes it necessary for there to be additional electrodes and measuring lines. WO 97/10013 describes a monitoring device based on the monitoring of the pressure in the extracorporeal blood circuit, in which the surges of pressure which are generated by the heartbeat and which are propagated along the flexible arterial and venous lines are detected. Absence of the pressure signals is considered to be an indication of faulty vascular access.

WO 2004/110528 A1 describes a device for checking an infusion pump which is based on the monitoring of the sound which the pump emits in operation, which can be sensed in the form of solid-borne sound or airborne sound. It is assumed in this case that, when operating properly, the pump emits sound which has certain characteristics. It is concluded that the pump's operation is faulty when the sound generated by it fails to show these characteristics. Faults with the drive, attributable for example to damaged bearings, can be detected in this way, but so too can blockages of the infusion catheter.

Known from U.S. Pat. No. 5,662,619 is a venous needle for patient access in an extracorporeal blood treatment. The venous needle is ground to a bevel at the distal end. To reduce turbulence as the blood emerges from the needle, lateral openings are provided in the needle and projections projecting into the lumen which point in the opposite direction to the direction of flow are provided downstream of the lateral openings.

SUMMARY OF THE INVENTION

The object underlying the present invention is to provide a device which allows an access to a patient, and in particular the venous access to a patient in extracorporeal blood treatment, to be safely and reliably monitored in an easy way.

A further object of the present invention is to provide an extracorporeal blood treating apparatus which has a monitoring device for the venous patient access which allows the access to be monitored safely and reliably in a simple way. It is also an object of the present invention to specify a method by which a patient access can be monitored with a high degree of safety and reliability in a simple way.

The device according to the present invention and the method according to the present invention for monitoring a patient access are based on the use of a special needle or cannula for the patient access. The needle or cannula is so designed that, due to the liquid flowing through the needle or cannula, air is drawn in if the needle or cannula is out of the vascular access. When air is drawn in with the needle or cannula out of the vascular access, sound is generated in turn. Therefore, a vascular access which is not in proper order can be detected with a high degree of certainty simply by monitoring the surrounding environment for the occurrence of sound.

It has been found that the drawing-in even of small amounts of air is able to produce a clearly audible noise when the needle or cannula is not in the vascular access. It is therefore possible for slipping of the needle or cannula out of the vascular access to be detected with a high degree of reliability.

However, for the signal to be analyzed, it is not necessary for the sound to be audible. Evidence of the sound may also manifest itself in the form of variations in pressure or density in an elastic medium, i.e. gases, liquids or solids, without the sound being audible. In this way, vibrations of solids may also be analyzed, e.g. by scanning their surface with a laser or by means of acceleration sensors, which may be mounted on the blood tubing for example.

The monitoring device according to the present invention is distinguished by the fact that it is easy to handle, inexpensive to manufacture and able to be retrofitted at any time. The monitoring device according to the present invention is used in particular to monitor the venous vascular access in an extracorporeal blood treatment. A further field of use is for monitoring a patient access in an infusion arrangement. In both these cases, a needle or cannula is used for the patient access.

A preferred embodiment of the monitoring device according to the present invention makes provision for the needle or cannula to have a narrowing of its cross-section and an opening. The needle or cannula thus constitutes a sort of venturi. The narrowing of the cross-section results in an increase in the dynamic pressure and a reduction in the static pressure at the point of narrowing. As a result, the speed of the liquid flowing through the needle or cannula rises in the region of the constricted portion of the needle or cannula, thus producing a pressure below atmospheric. Due to the pressure below atmospheric, air is drawn in through the opening in the needle or cannula, thus producing sound, if the needle or cannula is not properly seated in the patient's vessel.

Only one point of narrowing in the needle or cannula and only one opening are enough to generate sound of which evidence manifests itself reliably. It is however also possible for a plurality of points of narrowing or openings to be provided.

In a particularly preferred embodiment, the narrowing of the cross-section of the needle or cannula is produced by a constriction of the needle or cannula. It is however also possible for the point of narrowing to be formed by inwardly projecting projections.

In a particularly preferred embodiment of the needle or cannula, the opening is a through-hole in the constriction in the needle or cannula or an aperture milled through the wall of the needle or cannula. What is achieved in this way is that the air is drawn in in the region where the pressure below atmospheric is highest. It is however also possible for the opening to be arranged upstream or downstream of the point of narrowing in the direction of flow.

The monitoring device according to the present invention has an analyzing unit for sensing sound which is so designed that when sound is sensed it is concluded that a patient access is not in proper order.

The analyzing unit of the monitoring device according to the present invention preferably has a sound converter for converting sound signals into electrical signals which can be easily processed and analyzed by known electronic circuits. The sound converters which may be considered are all those by which sound signals can be converted into electrical signals. Examples of these are electrodynamic and capacitive sensors and ones which operate piezo-electrically or piezo-resistively.

The noise generated by the air which flows into the needle or cannula is transmitted not only by the audible airborne sound but also by the solid-borne sound which propagates in the liquid and in the adjoining flexible lines.

In another particularly preferred embodiment, provision is made for the solid-borne sound to be monitored to detect a vascular access which is not in proper order. In this embodiment, the analyzing unit has a converter of solid-borne sound for converting the solid-borne sound into electrical signals. What may be used as converters of solid-borne sound are for example piezo sound sensors or electret condenser microphones.

The converter of solid-borne sound is preferably arranged on the flexible line along which the solid-borne sound propagates. Permanent monitoring for the signal in the form of solid-borne sound permits a very short reaction time because the signal indicating a disruption occurs simultaneously with the disconnection of the needle or cannula.

However, in place of a converter of solid-borne sound, what may also be provided is a laser for scanning the surface of the flexible venous line or an acceleration sensor mounted on the flexible line, by which items variations in pressure or density can be detected.

The electrical signals which are generated by the sound converter or the laser for surface scanning or the acceleration sensor as a function of the variations in pressure or density may, be analyzed in different ways. In a preferred embodiment, it is the amplitude of the electrical signal which is monitored and which is compared with a preset reference signal. The analyzing unit concludes that a patient access is not in proper order if the electrical signal is higher than the reference signal. This makes it possible for the output signal to be distinguished reliably from interfering signals.

It is however also possible not only for the amplitude of the signal to be analyzed but also for the frequency of the signal to be taken into account in the analysis. In this way, typical sequences of sounds in the signal may be analyzed, which can first be filtered out of the signal. It is for example possible for a comparison to be made with a signal pattern which is characteristic of bubbles of air being drawn in. The signal processing can be performed by known analogue or digital techniques.

The monitoring device according to the present invention preferably has means which give an audio and/or visual alarm when it is detected that a patient access is not in proper order. As well as this, a signal for action to be taken in the control system of the blood treatment apparatus to interrupt the treatment of the blood may also be generated if it is detected that a patient access is not in proper order. The blood pump may be stopped for example and the flow of venous blood may be shut off by closing the venous tube clamp on the venous blood line of the extracorporeal blood circuit.

BRIEF DESCRIPTION OF THE DRAWINGS

An embodiment of the present invention will be explained below by reference to the drawings. In the drawings:

FIG. 2 shows the venous needle or cannula of the extracorporeal blood circuit of the extracorporeal blood treatment apparatus when there is an access to the venous vessel of the patient which is in proper order.

FIG. 3 is an enlarged view of the venous needle or cannula shown in FIG. 2.

FIG. 4 shows the output signal of the sound converter of the analyzing unit of the monitoring device according to the present invention when there is a vascular access in proper order.

FIG. 5 shows the venous needle or cannula when the vascular access is not in proper order.

FIG. 6 is an enlarged view of the cannula shown in FIG. 5.

FIG. 7 shows the output signal of the sound converter of the analyzing unit when there is a vascular access which is not in proper order.

DETAILED DESCRIPTION OF THE DRAWINGS

Figure 1:
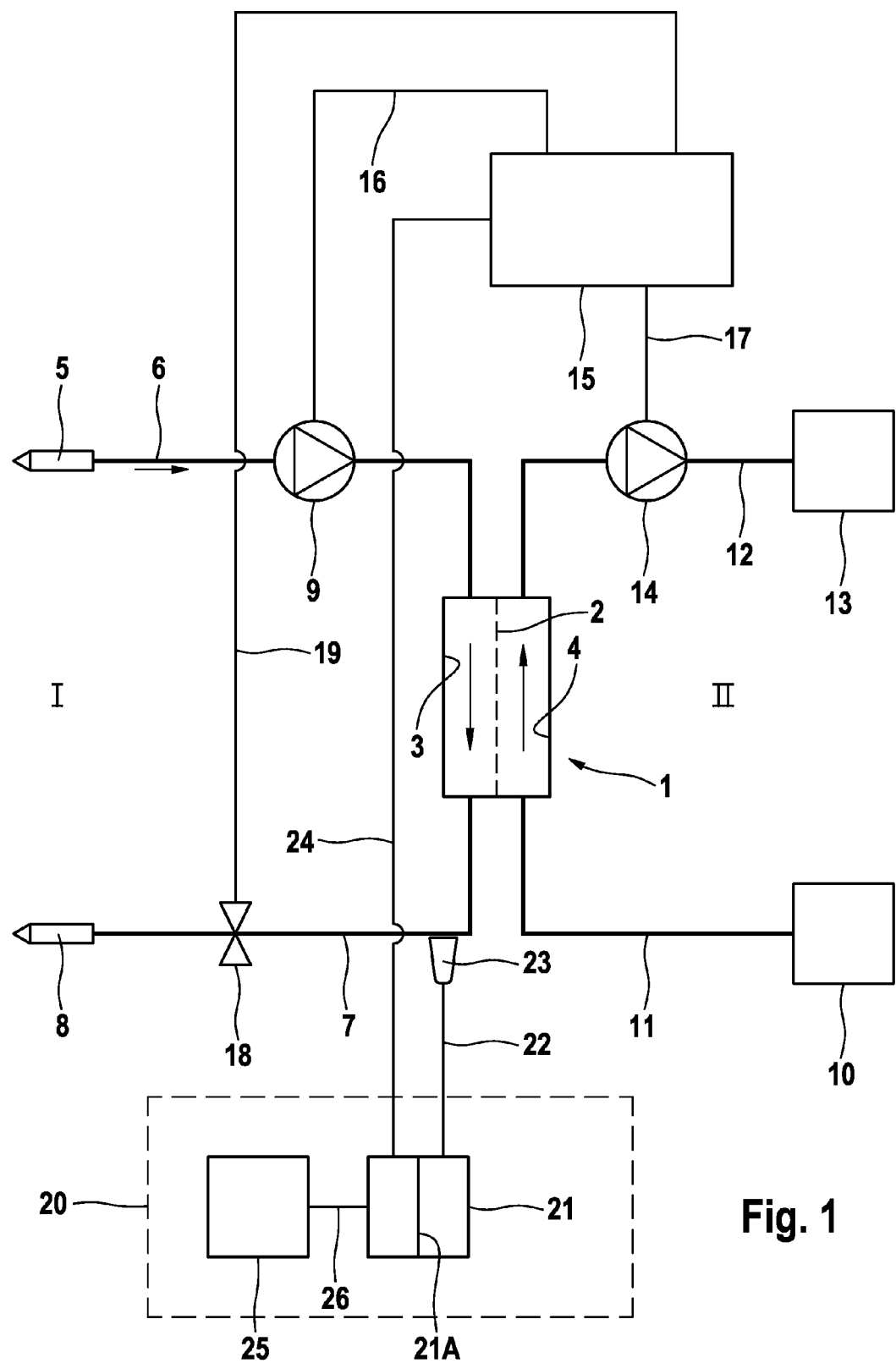
FIG. 1 is a highly simplified schematic view of the principal components of an extracorporeal blood treatment apparatus together with the device according to the present invention for monitoring the access to the patient.

FIG. 1 shows the principal components of an extracorporeal blood treatment apparatus, and in particular a hemodialysis apparatus, which has a device for monitoring the venous vascular access. The hemodialysis apparatus has a dialyser 1 which is divided into a blood chamber 3 and a dialysis-fluid chamber 4 by a semi-permeable membrane 2.

Connected to an artery of the patient by means of an arterial puncturing needle or cannula 5 is a flexible arterial line 6 which leads to the inlet to the blood chamber 3 of the dialyser. Running from the outlet of the blood chamber 3 of the dialyser 1 is a flexible venous line 7 which is connected to a vein of the patient by means of a venous puncturing needle or cannula 8. The flexible arterial line 6 is inserted into an occluding blood pump 9 which pumps the blood in the extracorporeal blood circuit 1.

The dialysis-fluid circuit II of the haemodialysis apparatus comprises a source 10 of dialysis fluid, to which is connected an inlet line 11 for dialysis fluid which leads to the inlet of the dialysis-fluid chamber 4 of the dialyser 1. Running from the outlet of the dialysis-fluid chamber 4 of the dialyser 1 is an outlet line 12 for dialysis fluid which leads to an outlet 13. Connected into the outlet line 12 for dialysis fluid is a dialysis-fluid pump 14 for pumping the dialysis fluid.

What is responsible for the control of the dialysis apparatus is a central control unit 15, which operates the blood and dialysis-fluid pumps 9, 14 via control lines 16, 17.

Downstream of the blood chamber 3 of the dialyser 1, on the flexible venous line 7, there is a tube clamp 18 able to be operated electromagnetically, which is closed by the central control unit 15, via a further control line 19, if the venous puncturing needle or cannula should happen to slip out of the vascular access. As well as this, the control unit 15 also stops the blood pump 9 if the cannula slips out.

To monitor the venous vascular access, there is provided a monitoring device 20 which may be an independent unit or part of the dialyser apparatus. In cases where a conventional dialyser apparatus is to be retrofitted with a device for monitoring the venous vascular access, the monitoring device 20 is an independent unit. Otherwise, the monitoring device is preferably part of the dialyser apparatus, because the dialyser apparatus already has various components which can be used by the monitoring device. These include for example the central controller (a microprocessor) of the dialyser apparatus and the power supply.

The monitoring device 20 has an analyzing unit 21 which is connected via a data line 22 to a sound converter 23 which measures solid-borne sound on the flexible venous line 7. However, in place of a converter of solid-borne sound there may also be provided a laser for scanning the surface of the flexible venous line or an acceleration sensor that is mounted on the flexible venous line, by which items vibrations can be detected. The analyzing unit 21 communicates with the central control unit 15 of the dialyser apparatus via a further data line 24.

The monitoring device 20 has an alarm unit 25 which is connected to the analyzing unit 21 via a data line 26. The alarm unit 25, which may also be the central alarm unit of the dialyser apparatus, generates an audio and/or visual alarm if the monitoring device 20 detects a venous vascular access which is not in proper order. If there is a vascular access which is not in proper order, the analyzing unit 21 also generates a control signal, which the central control unit 15 of the dialyser apparatus receives via the control line 24. When the central control unit 15 receives the control signal from the analyzing unit 21, the blood treatment is interrupted, in which case the control unit 15 closes the venous tube clamp 18 and stops the blood pump 9. FIGS. 2 and 3 show the venous puncturing needle or cannula 8 when there is a vascular access that is in proper order. Connecting to the needle or cannula is the flexible line 7 on which is mounted the converter 23 of solid-borne sound.

The needle or cannula is a conventional puncturing needle or cannula, but one which is of special design at the distal end.

To allow it to puncture the vessel 26, the needle or cannula has at the distal end a bevelled ground face 8A. When there is vascular access which is in proper order, i.e. when the needle or cannula has passed through into the vessel 26, blood flows out of the blood chamber 3 of the dialyser 1 through the lumen 8B of the needle or cannula and into the vessel 26 of the patient, while at the same time the patient's blood flows through the blood vessel 26. These flows of blood are indicated by arrows in FIGS. 2 and 3.

At the distal end, the needle or cannula 8 has a narrowing 8C which is formed by a constriction of a jet-like cross-section. The contour of the constriction 8C may for example be that of a venturi. In the region of the constriction 8C, the cross-section for flow is reduced by approximately 10 to 40%, and preferably 15 to 25%, relative to the diameter of the needle or cannula. Within the constriction 8C there is, in the wall of the needle or cannula, a through-hole 8D or a milled aperture through the wall of the needle or cannula. Because the constriction increases the resistance to flow, it should be made only sufficiently large to ensure that it performs its function.

In one embodiment, the outside diameter of the needle is 1.8 mm, the least outside diameter of the constriction is 1.5 mm, the length of the constriction is 2 mm and the diameter of the through-hole is 0.3 mm. The proportion which the constriction represents of the diameter of the needle is 16%.

The needle may for example be produced by impressing an all-round groove in the wall of a small thin-walled tube, by cold forming for example, so that the cross-section for flow becomes smaller. A suitable contour can be produced by selecting a suitable shape for the impressing tool.

Together with the constriction 8C, the through-hole 8D should be situated as close as possible to the beginning of the ground face 8A of the needle or cannula, thus ensuring on the one hand that, if the needle or cannula is properly seated in the patient's blood vessel, its lateral opening is always an adequate, safe distance away from the blood vessel, so that no air can be drawn in, and on the other hand that, if the needle withdraws, air is not drawn in until the needle has already slipped dangerously far out and there is a risk to the patient's life. In the embodiment, the hole 8D is situated on the opposite side from the tip of the needle or cannula.

Due to the reduction in the cross-section for flow, a pressure below atmospheric arises in the region of the constriction 8C and blood is thus drawn out of the vessel 26 into the needle or cannula. This blood then flows back out of the needle or cannula into the vessel. Because the diameter of the bore 8D is small, the additional flow of blood is relatively small or, depending on the conditions governing flow, and in particular due to blood's far greater viscosity than air, may not occur at all. This flow of blood is once again indicated by arrows in FIGS. 2 and 3.

FIG. 4 is a schematic representation of the electrical output signal from the converter 23 of solid-borne sound, which output signal the analyzing unit 21 of the monitoring device 20 receives. The electrical output signal has a DC component and an AC component. The AC component of the output signal is of only a very low amplitude attributable to interference signals because the needle or cannula is properly seated in the vessel (FIG. 2, FIG. 3).

FIGS. 5 and 6 show the case where the needle or cannula 8 has slipped out of the venous vessel 26. Because the needle or cannula is no longer in the vessel, ambient air is drawn in due to the pressure below atmospheric. The ambient air which is drawn in is expelled again with the blood that flows up. When this happens, sound is generated.

As well as being propagated as audible air-borne sound, the noise produced by the inflowing air is also propagated as solid-borne sound in the blood and in the blood line 7 which connects up with the needle or cannula. The converter 23 for solid-borne sound which is mounted on the flexible venous line 7 upstream of the needle or cannula 8 measures the solid-borne sound which occurs when the vascular access is not in proper order.

FIG. 7 is a schematic representation of the electrical output signal from the converter 23 for solid-borne sound. It can clearly be seen that, although the output signal has the same DC component as it has when there is a vascular access in proper order (FIG. 4), the AC component of the signal for solid-borne sound is of relatively large amplitude.

The analyzing unit 21 of the monitoring device 20 has a comparison unit 21A for comparing the amplitude of the AC component of the signal for solid-borne sound which is measured with a reference signal. The reference signal is of a size such that it is clearly above the level of the interference signals but is also below the level at which the AC component of the signal for solid-borne sound is situated when vascular access is not in proper order.

To detect the faulty vascular access, the analyzing unit may have means familiar to the person skilled in the art, such for example as a rectifier for rectifying the output signal and a comparator for making the comparison with the reference signal, or else filters etc.

If the AC component of the signal for solid-borne sound which is measured is higher than the reference level, it is concluded that there is faulty vascular access, i.e. it is concluded that the needle or cannula has slipped out of the vessel. The analyzing unit 21 then generates an alarm signal and the alarm unit 25 thus emits an audio and/or visual alarm and a control signal, thus causing the central control unit 15 of the dialysis apparatus to close the venous tube clamp 18, to stop the blood pump 9 and to interrupt the treatment. This prevents the free flow of blood, of which there would otherwise be a fear.

As the needle or cannula slips out of the blood vessel, then under certain conditions of flow a tiny jet of blood first comes out of the lateral hole, air not being drawn in until the ground face of the needle or cannula has withdrawn completely from the blood vessel, because the opposing pressure set up by the patient is then removed and the free flow takes place into the surrounding environment. Hence, air is not drawn in until the needle has withdrawn completely from the blood vessel.

In an alternative embodiment, the electrical signal from the converter 23 of solid-borne sound is compared in the analyzing unit 21 of the monitoring device 20 with a characteristic signal pattern which is characteristic of the sound which occurs on the needle or cannula slipping out. If the characteristic signal pattern is detected in the electrical signal from the converter 23 of solid-borne sound, the analyzing unit 21 concludes that there is a patient access which is not in proper order.

In the method according to the present invention, the sound signal is not generated until, and cannot be detected until, the needle or cannula has already slipped out of the vessel, meaning that blood treatment can no longer take place.

The invention claimed is:

1. A device for monitoring an access to a patient of an apparatus by which a liquid is provided to the patient via a needle or cannula comprising:
   a needle or cannula comprising a narrowed cross-section comprising a constriction for flow to generate a pressure below atmospheric due to the liquid flowing through the needle or cannula, wherein cross-sections on both sides of the narrowed cross-section are wider than the narrowed cross-section, said narrowed cross-section having an opening, the opening entirely within a region of the narrowed cross-section, the opening comprising a through-hole or a milled aperture within the constriction of the needle or cannula, and the needle or cannula being configured such that, if the needle or cannula is out of the access then, due to the liquid flowing through the needle or cannula, the needle or cannula draws in air through the opening, thereby causing a sound to be generated; and
   an analyzing unit for sensing the generated sound, said analyzing unit being configured such that, when the generated sound is sensed, it is determined that the patient access is not in proper order.

2. The device of claim 1, wherein the analyzing unit comprises:
   a sound converter for converting a sound signal into an electrical signal; or
   a laser for scanning a surface or an acceleration sensor which generate an electrical signal.

3. The device of claim 2, wherein the sound converter comprises a converter of solid-borne sound for converting solid-borne sound into electrical signals.

4. The device of claim 3, wherein the device is for monitoring the venous vascular access in the case of an extracorporeal blood treatment where blood is withdrawn from the patient via a flexible arterial line which has an arterial needle or cannula and blood is provided to the patient via a flexible venous line which has a venous needle or cannula, and
   wherein the converter of solid-borne sound is arranged on the flexible venous line to sense solid-borne sound which propagates along the flexible venous line.

5. The device of claim 2, wherein the analyzing unit comprises:
   a comparison unit for comparing an amplitude of the electrical signal with an amplitude of a preset reference signal, the analyzing unit being configured to determine that a patient access is not in proper order if the amplitude of the electrical signal is higher than the amplitude of the preset reference signal.

6. The device of claim 2, wherein the analyzing unit comprises:

a comparison unit for comparing the electrical signal with a characteristic signal pattern, the analyzing unit being configured to determine that a patient access is not in proper order if the characteristic signal pattern is detected in the electrical signal.

7. The device of claim 1, further comprising:
an alarm unit configured to give an audio and/or visual alarm if it is detected that a patient access is not in proper order.

8. A blood treatment apparatus having an extracorporeal blood circuit comprising:
a flexible arterial line having an arterial needle or cannula,
a flexible venous line having a venous needle or cannula, and
the device for monitoring the access to a patient of claim 1.

9. The device of claim 1, for monitoring the venous vascular access in the case of an extracorporeal blood treatment where blood is withdrawn from the patient via a flexible arterial line which has an arterial needle or cannula and blood is provided to the patient via a flexible venous line which has a venous needle or cannula, further comprising:
a control unit configured to generate a signal in a control system of a blood treatment apparatus to interrupt the treatment of the blood.

10. The device of claim 4, wherein the analyzing unit comprises:
a comparison unit for comparing an amplitude of the electrical signal with an amplitude of a preset reference signal, the analyzing unit being configured to determine that a patient access is not in proper order if the amplitude of the electrical signal is higher than the amplitude of the preset reference signal.

11. The device of claim 4, wherein the analyzing unit comprises:
a comparison unit for comparing the electrical signal with a characteristic signal pattern, the analyzing unit being configured to determine that a patient access is not in proper order if the characteristic signal pattern is detected in the electrical signal.

12. The device of claim 7, for monitoring the venous vascular access in the case of an extracorporeal blood treatment where blood is withdrawn from the patient via a flexible arterial line which has an arterial needle or cannula and blood is provided to the patient via a flexible venous line which has a venous needle or cannula, further comprising:
a control unit configured to generate a signal in a control system of a blood treatment apparatus to interrupt the treatment of the blood.

13. The device of claim 1, wherein the opening is in a surface of the needle or cannula which is not parallel to the narrowed cross-section.

* * * * *